United States Patent [19]

Blackwell, III et al.

[11] 4,252,742

[45] Feb. 24, 1981

[54] CHEMICAL PROCESS FOR THE PREPARATION OF 2,6-DIALKYLCYCLOHEXYLAMINES FROM 2,6-DIALKYLPHENOLS

[75] Inventors: Joseph T. Blackwell, III, Greensboro, N.C.; Henry C. Grace; James B. Nabors, both of Baton Rouge, La.; Harris E. Petree, Kernersville, N.C.

[73] Assignee: Ciba-Geigy Corporation, Ardsley, N.Y.

[21] Appl. No.: 56,164

[22] Filed: Jul. 13, 1979

[51] Int. Cl.³ .................... C07C 85/08; C07C 87/36; C07C 87/45
[52] U.S. Cl. .................................................. 564/447
[58] Field of Search .................................. 260/563 D

[56] References Cited

U.S. PATENT DOCUMENTS

| | | | |
|---|---|---|---|
| 3,272,865 | 9/1966 | Barker | 260/581 |
| 3,931,298 | 1/1976 | Wollensak | 260/581 |
| 3,994,975 | 11/1976 | Alink et al. | 260/563 D X |

*Primary Examiner*—Paul F. Shaver
*Attorney, Agent, or Firm*—Karl F. Jorda

[57] ABSTRACT

A process for preparing 2,6-dialkylcyclohexylamine, e.g., 2,6-dimethylcyclohexylamine, from a corresponding dialkylphenol, e.g., 2,6-dimethylphenol, by passing the phenol over a bed of a hydrogen-transfer catalyst in the presence of ammonia at elevated temperatures and pressures.

7 Claims, No Drawings

CHEMICAL PROCESS FOR THE PREPARATION OF 2,6-DIALKYLCYCLOHEXYLAMINES FROM 2,6-DIALKYLPHENOLS

FIELD OF THE INVENTION

This invention relates to a process for the production of certain dialkylcyclohexylamines from dialkylphenols. More particularly, this invention relates to the production of 2,6-dimethyl-, and 2-ethyl-6-methyl-, cyclohexylamine in good yield from the corresponding dialkylphenol.

BACKGROUND OF THE INVENTION

Dialkylcyclohexylamines are useful intermediates for the manufacture of economically important herbicides, fungicides, plant-growth regulants and other biologically active chemicals. Particularly useful as regards selectivity in action are the 2,6-dialkylcyclohexylamines where the alkyl moieties may be methyl or ethyl; both the same or either alkyl.

Typically such compounds, and more specifically 2,6-dimethylcyclohexylamine and 2-ethyl-6-methylcyclohexylamine, were previously prepared by the hydrogenation of the corresponding aniline or nitrobenzene, or by amination of the cyclohexanol or cyclohexanone. However, the 2,6-dialkyl derivatives of such compounds are not readily available. 2,6-Dimethylphenol is available in commercial quantities.

In the past, several methods have been devised for the conversion of phenols including alkylphenols to the corresponding anilines. The best of these are the catalytic methods, such as described in U.S. Pat. No. 3,931,298 describing the conversion of 2,6-dimethylphenol (2,6-DMP) to 2,6-dimethylaniline (2,6-DMA) in the presence of hydrogen, and ammonia over a hydrogen-transfer catalyst, preferably palladium, and a cyclohexanol as co-catalyst. As set forth therein the 2,6-DMP is converted to 2,6-DMA in yields of about 65 to 78%. The 2,6-dimethylcyclohexylamine (2,6-DMCHA) is reported in only trace amounts among the products.

U.S. Pat. No. 3,272,865 describes the direct amination by ammonia of certain specific phenols over Group 5B, 6 and 7B catalysts to the corresponding aniline. Dimethylphenols and dimethylanilines are not mentioned therein nor is there mention of the synthesis of presence of any cyclohexylamine among the products.

THE INVENTION

It is an object of this invention to provide a process for the manufacture of dialkylcyclohexylamines from dialkyl phenols in commercial quantities.

The process of this invention converts dialkylphenols (dialkyl hydroxybenzenes) to dialkylcyclohexylamines: e.g., 2,6-dimethylphenol (2,6-DMP) to 2,6-dimethylcyclohexylamine (2,6-DMCHA) and 2-ethyl-6-methylphenol (2,6-EMP) to 2-ethyl-6-methylcyclohexylamine (2,6-EMCHA) via the combined catalytic hydrogenation of the aromatic ring and amination of the resulting cyclohexyl moiety. The process can be carried out continuously over a broad range of temperatures, pressures and ratios of catalyst compositions.

More specifically, in the case of the conversion of 2,6-DMP to 2,6-DMCHA and 2,6-EMP to 2,6-EMCHA, the preferred conditions for the process of this invention encompass a temperature range of 150°–250° C.; a pressure range of 100–300 PSIG, a W/F ratio (wt. of catalyst) to weight of phenol per hour of >0.05–10; and gas concentrations of 5–20 moles of ammonia ($NH_3$) and 7–20 moles of hydrogen ($H_2$) per mole of the phenol. Suitable catalysts are platinum or palladium on inert supports.

Under optimal conditions and catalyst choice conversions of the phenol to the corresponding cyclohexylamine of greater than 99%, with selectivities to the desired cyclohexylamine of better than 95%, are realized.

Based on theoretical consideration and supported by detection of intermediates and partially reacted materials it appears that the reactions proceed as follows:

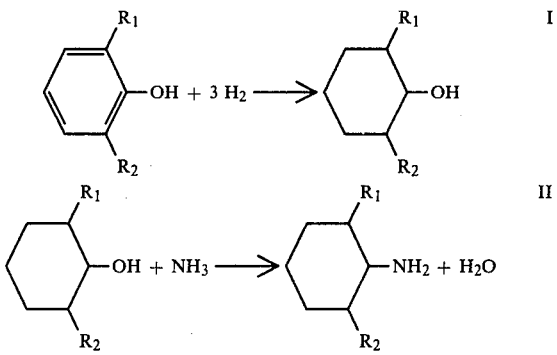

wherein $R_1$ and $R_2$ are each independently methyl or ethyl.

Depending on the reaction conditions, taking into consideration that both reactions are exothermic, when both $R_1$ and $R_2$ are methyl, the effluent from a continuous catalytic reactor as used for this process can be adjusted to vary with regard to the reaction components, intermediates and products. 2,6-Dimethylphenol (2,6-DMP), 2,6-dimethylcyclohexanol (2,6-DMCHOH) and 2,6-dimethylcyclohexylamine (2,6-DMCHA) are obtained under the preferred conditions. In practice at mild reaction conditions, small traces of 2,6-dimethylcyclohexanone have been noted due to incomplete hydrogenation. Also small amounts of unreacted 2,6-DMP and some 2,6-dimethylaniline have been noted.

The latter results from the reaction according to the following equation:

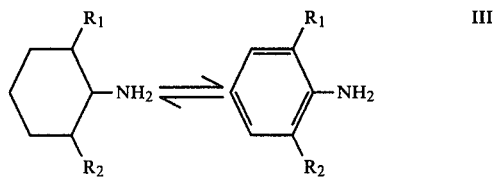

In view of the energy balance and the activity of the catalysts this reaction is to be expected.

The heats of the reaction of the 3 equations detailed above are as follows:

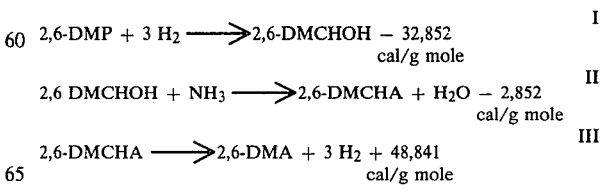

Consequently, the case of the overall reaction practiced in this invention:

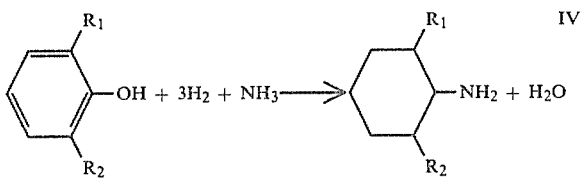

is fostered by the exothermic overall balance of reactions I and II. The total exotherm is $-33,604$ cal/g mole. Due to catalyst hydrogen-transfer activity and the reversability of the aromatization reaction (Equation III) at elevated temperatures and reduced pressures, the enthalpy balance favors this endothermic dehydrogenation reaction.

The preferred mode of the invention will be discussed with reference to the synthesis of 2,6-DMCHA from 2,6-DMP. Only minor adjustments in temperature, pressure, flow rate are needed to make it work with 2,6-EMP to form 2,6-EMCHA in the overall reaction of this invention (Equation IV).

The process of this invention is carried out in a single reactor provided with a tubular catalyst chamber and appropriate inlets and effluent ports. Preferred is the continuous flow, tubular trickle-bed type vessel fitted with inlets at the top for $NH_3$, $H_2$ and 2,6-DMP, and a knockout pot at the bottom.

The reactor chamber is packed with the catalyst and activated in a slow stream of $NH_3$ and $H_2$. Preferred activation temperatures are in the range 250°–300°.

The catalysts useful in this invention are those recognized as having high efficiency in hydrogen-transfer, selected from Group VIII elements supported on chemically inactive supports.

Good results are obtained with platinum and palladium supported on alumina and carbon. Preferred are 0.1 to 10% palladium catalysts supported on carbon or alumina granules. Platinum in the same range on carbon is as efficient, if the other factors such as temperature, contact-time and pressure are adjusted for their differences in hydrogen-transfer activity. Commercially available catalysts of these metals on the stated supports are active for the process of this invention with usual differences in activity between commercial sources.

With the preferred catalysts, the reactions are initiated at temperatures in the range 150° to 250° C. Within this range—with a preferred range of 175° to 225° C.—a minimum of unreacted 2,6-DMP and isomerism are obtained. Isomerism is the migration of the alkyl groups to other positions on the cyclic moiety-aromatic or cyclohexyl. Control of the temperature and W/F ratio within the preferred range provides good conversion and selectivity in the reaction.

Pressures in the range 100–300 PSIG are effective with pressures of about $200\pm25$ PSIG preferred. At these ranges for each mole of 2,6-DMP used, $NH_3$ and $H_2$ are used at levels of at least 5 but preferably 10 to 15 moles and up to 20 moles of each in the reaction feed.

The weight of catalyst (W) to weight of starting phenol, (2,6-DMP) passed over the catalyst per hour (F) should range between 0.05 and 10. This W/F ratio is varied with the activity of the catalyst. The more active the catalyst the lower the W/F value to be used. The lower values are achieved by mixing glass beads with the catalyst packed in the reactor vessel.

By adjusting the above factors, catalyst, temperature, pressure, W/F ratio and proper proportion of 2,6-DMP, $NH_3$ and $H_2$, continuous conversions of greater than 99%, based on 2,6-DMP and selectivity to 2,6-DMCHA of 80 to 97% are realized based on gas-liquid chromatographic (GLC) analysis.

The invention, in its preferred modes, will be discussed in the examples with reference to the conversion of 2,6-dimethylphenol to 2,6-dimethylcyclohexylamine but the conversion of 2-ethyl-6-methylphenol to 2-ethyl-6-methylcyclohexylamine is obtained within the described parameters with equivalent yields.

The appended examples illustrate the process of the invention according to preferred modes. While exemplary of the invention, they are not intended to limit the invention to the illustrated scope. The use of art-recognized equivalents is intended to be included. The limits of this invention are set forth in the appended claims.

DESCRIPTION OF EQUIPMENT

The continuous reactor used for the process of this invention is of the tubular trickle-bed type, fitted at the top with separate inlets for the phenol, $NH_3$ and $H_2$. The effluent collects in a knockout pot at the bottom. The reactor is fitted with a heater, appropriate temperature and pressure sensors and sampling tubes.

The catalyst, after being packed into the reactor, is activated by heating in a stream of $H_2$ and $NH_3$ for up to about 3 hours. Unless otherwise recommended by the commercial suppliers of the catalyst, activation is at 250° C. for two hours.

EXAMPLE 1

The reactor is packed with 0.5% Pt/carbon catalyst, and the catalyst is activated at 250° C. in a slow stream of $H_2$ and $NH_3$ for two hours. The temperature is then adjusted to 225° C., the pressure to 175 PSIG, and 2,6-DMP is passed over the catalyst at a W/F of 5.9. The mole ratio of $NH_3:H_2$:2,6-DMP is 10:15:1. The product obtained in the knockout pot when analyzed by GLC indicates a conversion of 99.9% and a selectivity of 79%.

EXAMPLE 2

The reactor is packed with 0.5% Pd/carbon catalyst, which is activated as in Example 1. The temperature is adjusted to 200° C., the pressure to 225 PSIG, and 2,6-DMP is passed over the catalyst at a W/F of 2.95. The mole ratio of $NH_3:H_2$:2,6-DMP is 15:15:1. The product obtained in the knockout pot when analyzed by GLC indicates a conversion of 99.9% and a selectivity of 97%. The reactor mass balance is 99.5%.

EXAMPLE 3

The reactor is packed with 1% Pd/alumina catalyst, activated as in Example 1. The temperature is adjusted to 200° C. and the pressure to 225 PSIG. The 2,6-DMP is passed over the catalyst at a W/F ratio of 6.5. The mole ratio of $NH_3:H_2$:2,6-DMP is 15:15:1. After a 29 hour run, the product obtained in the knockout pot, by GLC indicates a 97.48% conversion with 94.3% specificity to 2,6-DMCHA. The other components in the effluent in addition to the water were 0.79% 2,6-dimethylaniline, 1.34% 2,6-dimethylcyclohexanol and 0.15% dimethylcyclohexanone.

EXAMPLE 4

The reactor is packed with 0.5% Pd/carbon catalyst, which is activated as in Example 1. The temperature is adjusted to 200° C., the pressure to 225 PSIG, and 2- ethyl-6-methylphenol is passed over the catalyst at a W/F of 3.5. The mole ratio of NH$_3$:H$_2$:2-ethyl-6-methylphenol is 15:15:1. The product obtained in the knockout pot when analyzed by GLC indicates a conversion of 99.9% and a selectivity of 96.5%.

What is claimed is:

1. A method of preparing a 2,6-dialkylcyclohexylamine of the formula:

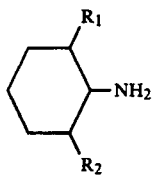

wherein R$_1$ and R$_2$ are each independently methyl or ethyl, which comprises the steps of passing a phenol of the formula:

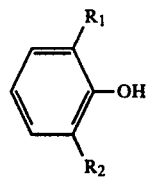

wherein R$_1$ and R$_2$ are as defined above, in contact with a bed of a hydrogen-transfer catalyst selected from the group consisting of the metals of Group VIII of the Periodic Table, in the presence of ammonia and hydrogen at temperatures in the range 150° to 250° C. and at pressures in the range 100 to 300 PSIG.

2. The process according to claim 1 wherein said catalyst is selected from the group consisting of platinum and palladium.

3. The process according to claim 1 wherein said phenol is selected from the group consisting of 2,6-dimethylphenol and 2-ethyl-6-methylphenol and the resulting cyclohexylamine is selected from the group consisting of 2,6-dimethylcyclohexylamine and 2-ethyl-6-methylcyclohexylamine.

4. The process according to claim 3 wherein said phenol is 2,6-dimethylphenol and said cyclohexylamine is 2,6-dimethylcyclohexylamine.

5. The process according to claim 2 wherein the ratio of the weight of the catalyst to the weight of the phenol passed per hour over the catalyst (W/F) is in the range 0.05 to 10.

6. The process according to claim 1 wherein the ratio of ammonia to said phenol ranges from 5:1 to 20:1, and the ratio of hydrogen to said phenol ranges from 5:1 to 20:1.

7. The process according to claim 4 wherein the 2,6-dimethylphenol is passed in contact with the catalyst consisting of 0.01 to 10% of platinum or palladium on a carbon or alumina support, at a pressure in the range 175 to 225 PSIG; a temperature in the range 175° to 225° C.; said 2,6-dimethylphenol being admixed with ammonia and hydrogen in ratios of 10 to 15 parts of ammonia and hydrogen per part of said phenol, said catalyst contacting being within the W/F ratio range of two to six.

* * * * *